United States Patent [19]
Goldberg et al.

[11] Patent Number: 5,701,083
[45] Date of Patent: Dec. 23, 1997

[54] APPARATUS FOR MEASURING CONSISTENCY AND FLOW RATE OF A SLURRY

[75] Inventors: Ira B. Goldberg, Thousand Oaks, Calif.; David L. Mays, Woodstock; Laurel A. Moormann, Roswell, both of Ga.

[73] Assignee: Allen-Bradley Company, Inc., Milwaukee, Wis.

[21] Appl. No.: 408,658

[22] Filed: Mar. 21, 1995

[51] Int. Cl.$^6$ .................................. G01N 22/04
[52] U.S. Cl. .................... 324/642; 324/640; 324/643; 73/861.06; 73/61.41
[58] Field of Search .................. 324/639, 642, 324/643; 73/861.05, 861.06, 861.07, 61.41

[56] References Cited

U.S. PATENT DOCUMENTS

| | | |
|---|---|---|
| 4,423,623 | 1/1984 | Ho et al. ............................ 73/61.41 |
| 4,674,325 | 6/1987 | Kiyobe et al. ..................... 324/640 X |
| 4,755,743 | 7/1988 | Jakkula ............................. 324/643 X |
| 4,888,547 | 12/1989 | McGinn et al. ..................... 73/861 |
| 5,324,485 | 6/1994 | White ................................ 422/159 |
| 5,331,284 | 7/1994 | Jean et al. ......................... 324/639 |
| 5,383,353 | 1/1995 | Marrelli et al. ................. 324/639 X |
| 5,455,516 | 10/1995 | Jean et al. ........................ 324/639 |

*Primary Examiner*—Ernest F. Karlsen
*Assistant Examiner*—Diep Do
*Attorney, Agent, or Firm*—Kyle Eppele; John M. Miller; John J. Horn

[57] ABSTRACT

A monitor for measuring physical parameters of a slurry, utilizing microwave propagation within a waveguide, either in conduit or a storage facility. Switching circuitry and specially constructed waveguides are provided, which operate in combination to provide rapid, accurate measurement of such parameters as flow rate, and concentration of the slurry.

8 Claims, 2 Drawing Sheets

APPARATUS FOR MEASURING CONSISTENCY AND FLOW RATE OF A SLURRY

FIELD OF THE INVENTION

This invention relates to the field of monitors, and particularly to monitors for measuring the concentration and flow rate of fluid mixtures.

BACKGROUND OF THE INVENTION

In order to control processes which utilize fluid mixtures of two materials, also referred to as a slurry, continuous or rapid monitoring of the concentration of the mixture and its flow rate is highly desirable. Examples of such processes include the disposal of sewage, the manufacture of paper from paper pulp, and coal water slurry transport systems for use in energy applications.

Because of the nature of many mixtures, most conventional measurement techniques are not completely satisfactory. The erosive nature of the flowing material precludes the use of devices that have moving parts or fragile components which must be immersed in the slurry. Instruments that require pressure transmission through fine openings or flow through small bypass tubes, have problems with clogging, caused by solid particles in the mixture or irreproducible sampling of the fluid through the orifice.

An example of a prior art monitor attempting to overcome the above-described problems is described in U.S. Pat. Nos. 4,888,547 and 4,423,623, which utilize microwave energy to determine the concentration and velocity of the fluid mixture, and are herein incorporated by reference. A prior art monitor uses a waveguide which contains the flowing mixture. The waveguide forms part of the conduit transporting the slurry and serves as a transmitting and receiving antenna for microwave signals of known characteristics. The flow rate of the mixture and concentration are correlated to the parameters of the received signal.

Unfortunately, such prior art monitors are ineffective in storage tank settings and sometimes suffer cross-talk errors between sensors in conduit environments. Accordingly, an improved apparatus free of the above limitations is needed.

SUMMARY OF THE INVENTION

The present invention is directed to an apparatus and a method of measuring certain objective parameters in a liquid mixture or slurry. In one form, the invention comprises at least two sensors, either immersed in the slurry, or forming a portion of the slurry container, an RF signal source, a processor coupled to the storage device, electrical circuitry coupling each of the aforementioned elements, so that sensed data is provided to the processor for derivation of such objective slurry parameters as concentration or flow rate.

In one embodiment of the invention, an RF signal source is coupled to a splitter, which in turn, provides a power signal to an attenuator. An output signal of the attenuator is coupled to a directional coupler and on to a sensor. An output signal from the sensor is coupled, via directional coupler, through amplifying stages, as needed, and onto the processor. Similar channels are provided for each sensor. The processor evaluates measured signals in a predetermined manner, while also providing control signals to a switch that is strategically commanding the electrical channels. By measuring the dielectric constant of the slurry, with the above-described circuitry, the consistency of the mixture is determined by the processor.

Alternate embodiments of the above apparatus include the use of a slotted clamshell or basket sensor, as described hereinafter. Circuit simplicity is possible, dependent upon design parameters and the frequency needed in obtaining measurements.

It is an object of the present invention to provide an apparatus for measuring the composition and velocity and temperature of a liquid mixture.

It is a feature of the present invention to utilize at least two sensors, electrically coupled in combination to a processor.

It is an advantage of the present invention to provide an apparatus that can measure the composition of a liquid mixture in a storage tank or a pipe.

These and other objects, features and advantages are disclosed and claimed in the specification, figures and claims of the present application.

DESCRIPTION OF THE PREFERRED EMBODIMENT

Figure 1:
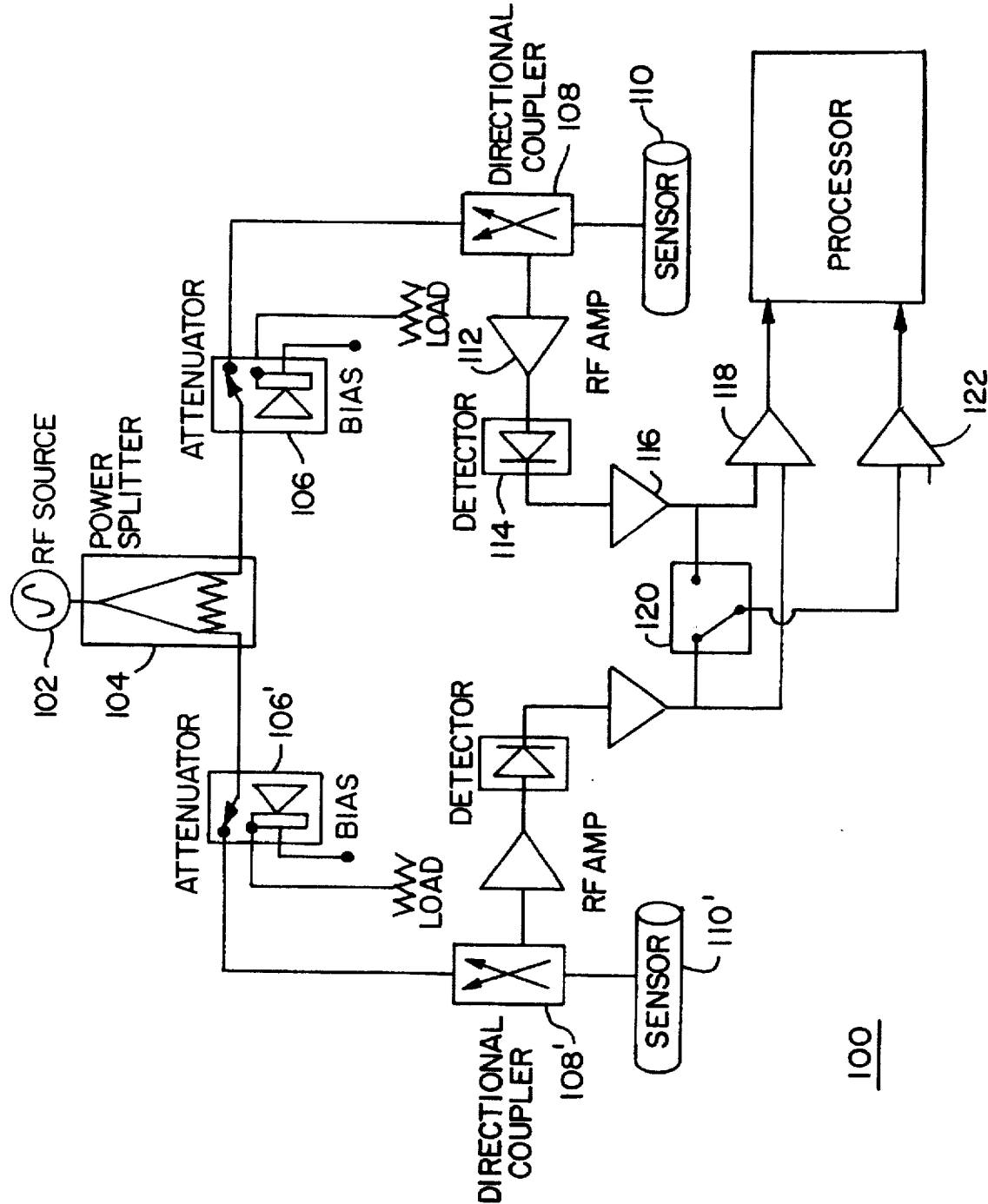
FIG. 1 is a block diagram of one embodiment of an apparatus incorporating the teachings of the present invention.

Turning now to the drawings, wherein like items are referenced as such throughout. FIG. 1 illustrates a block diagram of one embodiment of the flow monitor 100 of the present invention. A signal source 102 is shown electrically coupled to a signal splitter 104, through an attenuator 106, such as a PIN diode attenuator, a directional coupler 108, and on to a sensor 110. The directional coupler 108 is also coupled to a first amplifier 112, and on to a detector 114, a second amplifier 116, and a differential operational amplifier 118. A similar channel is shown for sensor 110'. Additionally, a switch 120 is coupled in parallel to the output signal of each of the amplifiers 116, 116', for purposes of single channel measurement.

The functional operation of the circuit of FIG. 1 will now be described. An RF power signal from source 102 is split and coupled to electronic attenuators 106 (106'), that are bias voltage controlled. The PIN diode attenuator 106 (106') can be used to regulate the amplitude of the signal at the detector 114 (114') or to activate and deactivate the sensor 110 (110'). The split signal may then be directed to either, or both of sensors 110 (110') via the previously described directional coupler. The directional coupler 108 (108') samples the reflected power from the sensor 110 (110'). A portion of the reflected power signal is coupled to the detector 114, and subsequently on to the operational amplifier 118, and on to additional processing means 124.

Figure 2:
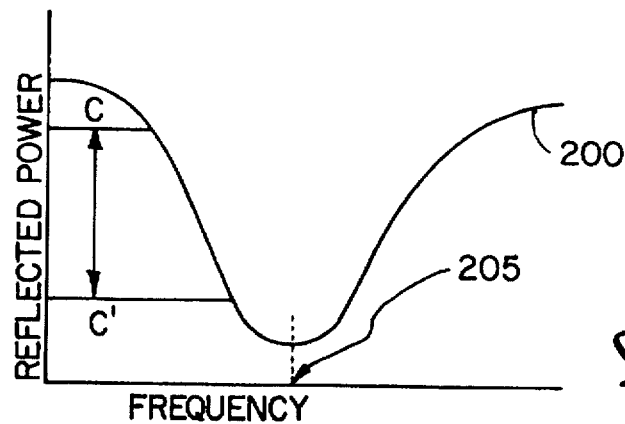
FIG. 2 is a graph showing the relationship of reflected power to signal power for a typical embodiment of the apparatus in FIG. 1.

FIG. 2 illustrates a graphical illustration of a typical two dimensional curve 200, of the reflected power signal to the signal frequency. The point on curve 200, represented by 205, is a frequency that can be used to measure the dielectric constant of the fluid in the sensor 110 (110') and is called the characteristic frequency. In order to diminish the effects of cross-talk interference between the sensors and detectors, the channels are alternatively activated at different time intervals. The reflected power, or characteristic frequency is measured for one sensor 110, the circuit is switched, via switching means 120, and the measurement is repeated on the other sensor 110'. It is only necessary to store one data point for each channel. Either the characteristic frequency, or the amplitude of the reflected power at a given frequency may be used as the single data point for each channel. If the characteristic frequency is used, it may be selected from the scan of the reflected power versus frequency, and only the single point value retained for correlation purposes.

An alternate embodiment of the above configuration would be elimination of one of the channels, associated electronic circuitry and switching the signal between the sensors 110 and 110'. This implementation would require the use of mechanical switches, that provide no directionality to power flow. Such switches often prove less reliable than electronic switches when used for long periods of time, or after numerous switching events, and may be slow as contrasted to solid state devices. In addition to the increased speed of solid state switches, they typically provide superior isolation of the input from the output signal, such that power can only flow in one direction. Consequently, a minimum of two directional couplers are recommended. By inserting a second solid state switch, the signal source 102, detector 114, amplifier 112, could be common to both sensors. In such instances not requiring an RF amplifier, a detector could be used with each directional coupler and a low frequency switch rather than a high frequency device that could be inserted so that the low frequency components are common to both sensors 110 and 110'.

Figure 3:
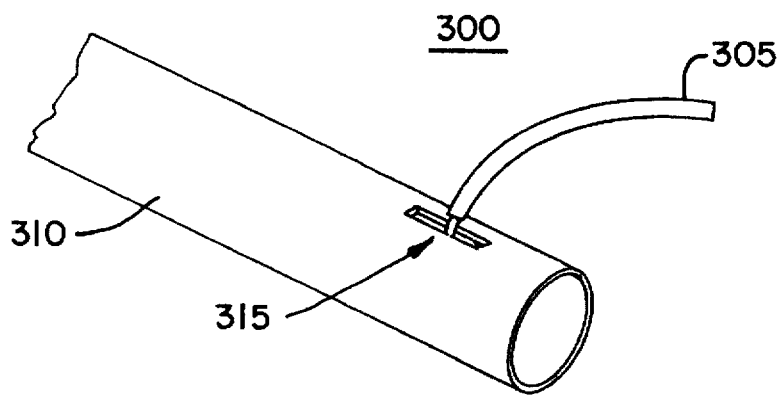
FIG. 3 is a perspective view of one embodiment of a suitable sensor for the apparatus of FIG. 1.
Figure 4:
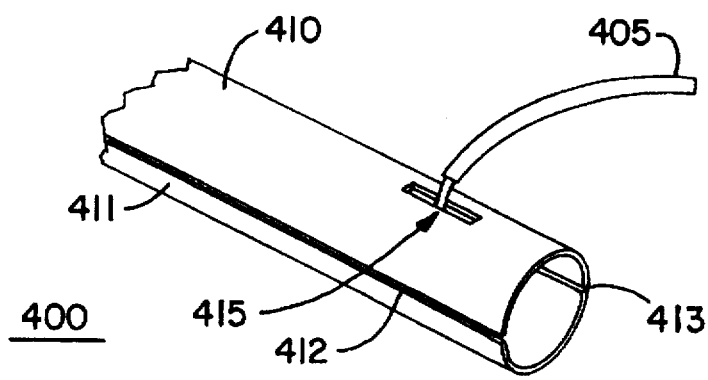
FIG. 4 is a perspective view of an alternate embodiment of the sensor of FIG. 3.

The sensor 110 described in FIG. 1 may be implemented in a variety of ways as determined by application design requirements. FIGS. 3 and 4 are illustrative of alternate embodiments suitable for use in monitor 100 (see FIG. 1). The sensor 300 of FIG. 3, is a slotted metallic pipe sensor of variable length, diameter, and wall thickness. A coaxial cable 305 is electrically coupled to tubular shell 310 of the sensor 300 at slot 315. The slot 315 is filled with a dielectric material that exhibits low loss at the signal of interest. The purpose of the coaxial cable 305 coupled to the slot 315 is to inject a radio frequency signal into the tubular section 310, which then acts as a waveguide to carry the signal for measuring the characteristics of the slurry flowing within it.

FIG. 4 depicts a metallic clamshell sensor 400, also of variable dimensions, suitable for use in monitor 100 (FIG. 1). The sensor 400 is comprised of two symmetrical halves 410, 411 having longitudinal seams 412, 413. Each half 410, 411 is electrically insulated from the other half, thereby only allowing TM mode signals to be propagated. By constructing the sensor 400 to only support TM mode signal propagation, signal interference from other modes are thereby eliminated. RF signal injection and slurry characteristics are determined as set forth below. The clamshell design permits the sensor to be used when the slurry is transported through a non-conductive pipe or tube such as plastic or glass. In this embodiment, the clamshell is place around the pipe containing the slurry. This permits the sensor to be installed without interrupting the fluid transport.

For purposes of measuring mixture concentration, a single sensor may be used. The characteristic frequency 205 provides a measure of the concentration of one component of the slurry. As the concentration of the slurry changes, the entire curve 200 shifts to the right (or left) with respect to the X axis, depending upon the dielectric constants of the different components of the slurry and the resultant concentration. The calibration of the characteristic frequency for sensor 400 as a function of the slurry concentration will differ from the calibration of the slotted metallic pipe sensor 300 of the same diameter because of the selection of the TM mode and the presence of the pipe or tube.

Flow rate determinations, however, require that signals from both sensors 110 (100') be cross-correlated. Either the characteristic frequency, or the amplitude of reflected power at a given frequency can be used for the correlation procedure. Since the curve 200 changes position on the X axis, as the slurry concentration varies, in both the reflected power when measured at a fixed frequency, either parameter may be used for cross-correlation.

If reflected power measurements are used for correlation, the frequency at which data is collected can be preset, or selected from the optimal range (C-C') of curve 200. Utilizing the amplitude of the reflected power at a selected frequency would provide greater dynamic range, but use of characteristic frequency may be easier to implement. Additionally, if cross-talk is not a problem, then auto-correlating the difference between the detected reflected power from both channels may be measured with the differential amplifier 118 (see FIG. 1), thereby providing greater dynamic range and corresponding sensitivity.

While particular embodiments of the present invention have been shown and described, it should be clear that changes and modifications may be made to such embodiments without departing from the true scope and spirit of the invention. It is intended that the appended claims cover all such changes and modifications.

We claim:

1. A flow monitor for measuring the rate of flow of a slurry comprising:

two slotted waveguide sensors immersible in a slurry to be measured, each sensor comprising a transmitting antenna and a receiving antenna:

an RF signal source;

switching circuitry coupled to the RF signal source and each sensor;

wherein the switching circuitry is comprised of a plurality of channels, each channel comprising:

an attenuator;

a directional coupler disposed between and coupled to the attenuator and the sensor;

an amplifier coupled to the directional coupler;

a detector coupled to the amplifier;

a switch for activating any or all channels and further coupling an output signal to the processor; and a processor coupled to the switching circuitry for correlating the sensed data dielectric constant from each sensor and providing control signals to the switching circuitry.

2. The monitor of claim 1, wherein the attenuator is a PIN diode type device.

3. The monitor of claim 1, further including amplifier having as its input signal, the output signal of the detector and having its output signal coupled to each of the switch and additional processing means.

4. The monitor of claim 3, further including a signal splitter coupled to the RF signal source and each attenuator.

5. A flow monitor for measuring consistency of a slurry while the slurry is being transported through non-conductive piping comprising:

two metallic clamshell waveguide sensors coupled externally to the piping containing the slurry;

an RF signal source;

switching circuitry coupled to the RF signal source and each sensor:

a processor coupled to the switching circuitry for correlating the sensed data dielectric constant and providing control signals to the switching circuit;

wherein the switching circuitry is comprised of a plurality of channels, each channel comprising:

an attenuator;

a directional coupler disposed between and coupled to the attenuator and the sensor;

an amplifier coupled to the directional coupler;

a detector coupled to the amplifier; and a switch for activating any or all channels and further coupling an output signal to the processor.

6. The monitor of claim 5, wherein the attenuator is a PIN diode type device.

7. The monitor of claim 5, further including an amplifier having as its input signal, the output signal of the detector and having its output signal coupled to each of the switch and additional processing means.

8. The monitor of claim 7, further including a signal splitter coupled to the RF signal source and each attenuator.

* * * * *